(12) United States Patent
Grate et al.

(10) Patent No.: US 7,430,928 B2
(45) Date of Patent: Oct. 7, 2008

(54) METHOD AND APPARATUS FOR CONCENTRATING VAPORS FOR ANALYSIS

(75) Inventors: Jay W. Grate, West Richland, WA (US); David L. Baldwin, Kennewick, WA (US); Norman C. Anheier, Jr., Richland, WA (US)

(73) Assignee: Battelle Memorial Insititute, Richland, WA (US)

( * ) Notice: Subject to any disclaimer, the term of this patent is extended or adjusted under 35 U.S.C. 154(b) by 296 days.

(21) Appl. No.: 11/350,716

(22) Filed: Feb. 8, 2006

(65) Prior Publication Data

US 2007/0180933 A1    Aug. 9, 2007

(51) Int. Cl.
  *G01N 1/00* (2006.01)
(52) U.S. Cl. .................................. 73/863.21
(58) Field of Classification Search ........................ None
  See application file for complete search history.

(56) References Cited

U.S. PATENT DOCUMENTS

| | | | |
|---|---|---|---|
| 4,607,604 A * | 8/1986 | Kanoh et al. ................. | 123/572 |
| 5,550,062 A | 8/1996 | Wohltjen et al. | |
| 6,221,673 B1 | 4/2001 | Snow et al. | |
| 6,585,111 B1 * | 7/2003 | Shervington et al. ......... | 206/0.7 |
| 6,652,627 B1 * | 11/2003 | Tonkovich et al. ............ | 95/104 |
| 6,824,592 B2 * | 11/2004 | Monzyk et al. .................. | 96/4 |
| 6,881,585 B1 | 4/2005 | Potyrailo et al. | |
| 6,902,701 B1 | 6/2005 | Hughes et al. | |
| 6,914,220 B2 | 7/2005 | Tian et al. | |
| RE38,797 E | 9/2005 | Linker et al. | |
| 2003/0145726 A1 * | 8/2003 | Gueret et al. ................... | 95/96 |
| 2004/0112211 A1 * | 6/2004 | Meirav ............................ | 95/8 |
| 2004/0131503 A1 * | 7/2004 | McGann et al. ............... | 422/99 |
| 2004/0191122 A1 | 9/2004 | Potyrailo et al. | |
| 2005/0079626 A1 | 4/2005 | Kunz | |
| 2005/0098033 A1 * | 5/2005 | Mallavarapu et al. .......... | 95/96 |
| 2005/0210957 A1 | 9/2005 | Tipler et al. | |

FOREIGN PATENT DOCUMENTS

EP    1 405 988    *   7/2003

OTHER PUBLICATIONS

Giddings, et al., Unified Separation Science, John Wiley and Sons, New York, 1991 (Book).
Mitra, et al., J. Chromatogr., 1993.
Kindlund, et al., Sens. Actuators, 1984, 6, pp. 1-17.
Mitra, et al., Rev. Sci. Instrum., 1988, 59, pp. 1427-1428.
Mitra, et al., J. Chromatogr. Sci., 1995, 33, pp. 285-289.

(Continued)

*Primary Examiner*—Robert R Raevis
(74) *Attorney, Agent, or Firm*—James D. Matheson

(57) ABSTRACT

An apparatus and method are disclosed for pre-concentrating gaseous vapors for analysis. The invention finds application in conjunction with, e.g., analytical instruments where low detection limits for gaseous vapors are desirable. Vapors sorbed and concentrated within the bed of the apparatus can be thermally desorbed achieving at least partial separation of vapor mixtures. The apparatus is suitable, e.g., for preconcentration and sample injection, and provides greater resolution of peaks for vapors within vapor mixtures, yielding detection levels that are 10-10,000 times better than for direct sampling and analysis systems. Features are particularly useful for continuous unattended monitoring applications.

12 Claims, 9 Drawing Sheets

OTHER PUBLICATIONS

Mitra, et al., J. Chromatogr., A, 1996, vol. 736, pp. 165-173.
Mitra, et al., J. Chromatogr., A, 1996, vol. 727, pp. 111-118.
Feng, et al., J. Chromatogr., A, 1998, vol. 805, pp. 169-176.
Mitra, et al., J. Mass Spectrom, 1999, vol. 34, pp. 478-485.
Feng, J. Microcolumn Separations, 2000, vol. 12, pp. 267-275.
Kim, et al., J. Chromatogr., A, 2003, vol. 996, pp. 1-11.
Groves, et al., Am. Ind. Hyg. Assoc. J., 1996, vol. 57, #11, pp. 1103-1108.
Groves, et al., C. Anal Chim. Acta, 1998, vol. 371, pp. 131-143.
Shaffer, et al., Field Anal. Chem. Technol., 1998, vol. 2, pp. 179-192.
Heller, et al., Proc-Electochem Soc.-Chemical Sensors IV, 1999, 99-23, 138-142.
Cai, et al., Sens. Actuators, 2000, B62, pp. 121-130.
Nakamoto, et al., Sens. Actuators, B, 2000, B69, pp. 58-62.
Nakamoto, et al., IEEE Sensors Journal, 2004.
Park, et al., Analyst (Cambridge, United Kingdom) 2000, 125, pp. 1775-1782.
Park, et al., AIHAJ, 2000, vol. 61, pp. 192-204.
Groves, et al., Annals of Occupational Hygiene, 2001, vol. 45, pp. 609-623.
Hughes, et al., Proceedins-Electrochemical Society, 2001, vol. 18, pp. 348-354.
Lu, et al., Anal. Chem, 2001, vol. 73, pp. 3449-3457.
Lu, et al., Analyst (Cambridge, United Kingdom), 2002, vol. 127, pp. 1061-1068.
Morris, et al., Meas. Sci. technol., 2002, vol. 13, pp. 603-612.
Bender, et al, Sens. Actuators, 2003, vol. B93, pp. 135-141.
Hamacher, et al., Sens. Actuators, B, 2003, B95, pp. 39-45.
Zellers, et al., Sens. Actuators, B, 2000, B67, pp. 244-253.
Tian, et al, Microelectromechanical Systems, 2003, 12, pp. 264-272.
Dworzanski, et al, Anal. Chim. Acta, 1994, vol. 293, pp. 219-235.
Nakamoto, et al., Proceedings of IEEE Sensors, 2002, IEEE International Conf. on Sensors, 1st, Orlando, FL, Jun. 12-14, 2002, vol. 1, pp. 366-371.
Nakamoto, et al., Sens. Actuators, 2003, vol. B89, pp. 285-291.
Booksh, et al, Anal. Chem., 1994, vol. 66, pp. 782A-791A.
Wenzel, et al., IEEE Trans, Electro Devices, 1988, vol. 35, pp. 735-743.
Wenzel, et al, Appl. Phys. Lett., 1989, vol. 54, pp. 1976-1978.
Wang, et al, Electron. Lett., 1990, vol. 26, pp. 1511-1513.
Wenzel, et al., Sens. Actuators, 1990, vol. A21-A23, pp. 700-703.
Grate, et al., Anal. Chem., 1991, vol. 63, pp. 1552-1561.
Grate, et al., Chemical Innovations, 2000, vol. 30 (11), pp. 29-37.
Rood, A Practical Guide to the Care, Maintenance, and Troubleshooting of Capillary gas Chromatographic Systems; 3rd Revised Ed.; Wiley, 1999, pp. 32-33.
Jeansonne, J. Chromatogr. Sco, 1991, vol. 29, pp. 258-266.
Jeansonne, J. Chromatogr. 1992, vol. 594, pp. 1-8.
Gargallo et al., TrAC, Trends Anal. Chem., 1996, vol. 15, pp. 279-286.
Osten, et al., Anal. Chem., 1984, vol. 56, pp. 991-995.
Rodriguez-Cuesta, et al., Anal. Chem. Acta,, 2003, vol. 476, pp. 111-122.
Strasters, et al., Anal. Chem., 1988, vol. 60, pp. 2745-2751.
Tauler, et al., Chemom. Intel Lab Sys., 1995, vol. 30, pp. 133-146.
Grate, et al., Anal. Chem. 1999, vol. 71, pp. 4544-4553.
Grate, et al., Anal. Chem. 2001, vol. 73, pp. 2239-2244.
Grate, et al., Anal. Chem. 2001, vol. 73, pp. 5247-5259.
Wise, et al., Chemometrics, 2003, vol. 17, pp. 463-469.
Grate, et al., Anal. Chim. Acta, 2003, vol. 490, pp. 169-184.
Grate, et al., Anal. Chem. 1993, 65, pp. 1868-1881.

* cited by examiner

METHOD AND APPARATUS FOR CONCENTRATING VAPORS FOR ANALYSIS

This invention was made with Government support under Contract DE-AC05-76RLO1830 awarded by the U.S. Department of Energy. The Government has certain rights in the invention.

FIELD OF THE INVENTION

The present invention relates generally to a method and apparatus for concentrating gaseous vapors for analysis. The invention finds application in conjunction with, e.g., analytical instruments where low detection limits for gaseous vapors are desirable or where preseparation of vapors is desirable.

SUMMARY OF THE INVENTION

In one aspect, the invention is an apparatus for concentrating vapors for analysis, comprising: a conduit having at least one inlet and one outlet for flowing one or more vapors in a gaseous volume therethrough, said conduit containing a sorbent for concentrating vapors from said gaseous volume by sorption, wherein said sorbent is operatively disposed within a metal foam. Typically a heater, or a heater and a temperature sensor, is operatively disposed to heat the conduit, metal foam and the sorbent, which enables thermal desorption of vapors from the sorbent.

The metal foam provides a high thermal conductivity medium in which the sorbent is operatively disposed, so that when heat is applied to desorb vapors from the sorbent, the heat can travel rapidly from the periphery of the conduit to the center. In this way, the entire sorbent bed can be heated more rapidly than would be observed if the metal foam were not present. For example, many sorbent materials are poor conductors of heat, so that the center of a sorbent bed heats up more slowly than the periphery when heat is applied to the periphery. Nonuniform heating can degrade the desired performance of a preconcentrator. In one method of use, a vapor preconcentrator, after collecting vapors on the sorbent, is heated as rapidly as possible to desorb the collected vapors as a single brief pulse resulting in a tall, sharp peak in the detected concentration of the vapor. In this method, it is desirable that the entire bed of sorbent is heated as rapidly as possible. The presence of the metal foam can increase the rate of heating of the center of the sorbent bed thereby providing more rapid heating of the entire bed, and a sharper taller peak in the resulting vapor concentration. If this vapor is delivered directly to a detector, the peak is taller, providing better sensitivity and lower detection limits. If the vapor is delivered to a gas chromatograph, the shorter pulse of vapor at higher concentration provides a shorter injection time and hence reduces band broadening due to injection.

In another method of using a preconcentrator, the heat is delivered to the sorbent more gradually, raising the temperature at a slower controlled rate. This provides a controlled thermal desorption of the vapors, in which some vapors may be desorbed at lower temperatures than others, resulting in a separation or partial separation of vapor mixtures. If heat transfer within the sorbent bed is poor, the periphery will heat faster than the center of the bed, and hence some regions of the bed will be at different temperatures than other regions of the bed. This will result in a longer period of time during which a vapor is desorbed, yielding a broader desorption peak. When a mixture of vapors is desorbed under these conditions, the broader peaks will lead to poorer separation and resolution of the individual vapors. By including a metal foam in the design, the thermal desorption process occurs with better temperature uniformity thoughout the sorbent bed. When the entire bed is at or near the same temperature at the same time during the thermal desorption process, the desorption peaks will be narrower and individual vapors better separated and resolved.

So, whether one is heating the preconcentrator as rapidly as possible, or heating at a slower controlled rate for a gradual thermal desorption, the inclusion of the metal foam in the preconcentrator to provide more rapid and uniform heating of the entire bed volume is advantageous. Because metal foam is porous, the sorbent can be disposed within the pores and gases can flow therethrough. In fact, metal foam can be 95% or more empty space by volume, providing an excellent flow through medium with excellent thermal conductivity, in which sorbent material can be placed and gases can flow through.

In another aspect, the invention is a process for preconcentrating vapors in a gaseous volume for analysis, comprising: providing a conduit having at least one inlet and one outlet for flowing one or more vapors in a gaseous volume therethrough, said conduit containing a sorbent for concentrating vapors from said gaseous volume by sorption, wherein said sorbent is operatively disposed within a metal foam; sorbing the one or more vapors on the sorbent thereby concentrating the one or more vapors; and heating the sorbent to a temperature sufficient to desorb the one or more concentrated vapors therefrom, generating a peak response in a detector of sufficient sensitivity for detection and/or analysis of the one or more concentrated vapors.

In another aspect, the rate of thermal desorption is controlled to provide at least partial separation of the one or more vapors generating a peak response in a detector of sufficient sensitivity for detection and/or analysis of the one or more concentrated vapors.

In an embodiment, the conduit is a flow-through channel enclosed within a tube.

In another embodiment, a flow-through channel is a machined channel.

In another embodiment, the metal foam comprises nickel.

In another embodiment, the metal foam comprises stainless steel.

In another embodiment, the metal foam has a mean pore diameter of about 380 microns.

In another embodiment, the metal foam comprises at least about 95% air by volume.

In another embodiment, the sorbent is of a mesh size selected in the range from about 60 to about 80.

In another embodiment, the sorbent is of a grain size selected in the range from about 170 microns to about 250 microns.

In another embodiment, the sorbent is selected from the group of Tenax®, Carbotrap, Carboxen, Carbosieve, glass bead), polymers, molecular sieves, activated carbons, carbon nanotubes, ceramics, Aluminas, Silicas, silica gels, polars, dessicants, or combinations thereof, or the like.

In another embodiment, the apparatus is operatively disposed to a detector for measuring said one or more vapors desorbed therefrom.

In another embodiment, the apparatus is operatively disposed to a detector selected from the group consisting of Surface Acoustic Wave sensor, Flexural Plate Wave Sensor, mass spectrometer, ion mobility spectrometer, gas chromatograph, sensor array, multivariate detector, flame ionization detector, chemical sensor, or the like, or combinations thereof.

In another embodiment, the apparatus comprises a heater and a temperature sensor operatively disposed for controlled thermal desorption of said one or more vapors concentrated therein.

In another embodiment, thermal desorption of said one or more vapors is effected in conjunction with temperature programming and/or thermal ramping.

In another embodiment, the apparatus further comprises a detector for analysis of the one or more vapors desorbed therefrom selected from the group consisting of sensor arrays, chemical sensors, mass spectrometers, ion mobility spectrometers, gas-chromatography detectors, or the like, or combinations thereof.

In another embodiment, the apparatus includes a gas chromatography detector selected from the group consisting of thermal conductivity detectors, electron capture detectors, flame ionization detectors, or the like, or combinations thereof.

In another embodiment, sorption and desorption of said one or more vapors occurs without altering composition of said vapors.

In another embodiment, the preconcentrator provides an improvement in detection limit by a factor in the range from about 10 times to about 10,000 times over that for a direct sampling and analysis system.

In another embodiment, the metal foam provides sufficient thermal conductivity to said conduit upon heating achieving essentially uniform temperatures for rapid thermal desorption of said one or more vapors concentrated therein; and whereby desorption of said one or more concentrated vapors from said sorbent within said foam provides sufficiently high sensitivity for detection of said one or more concentrated vapors.

In another embodiment, the sorption of said one or more vapors comprises flowing said gaseous volume through said conduit at a rate in the range from about 1 mL/min to about 10,000 mL/min for a period of time.

In another embodiment, heating of said sorbent is effected in conjunction with use of a heater and a temperature sensor operatively disposed within said conduit for effecting controlled thermal desorption of said one or more vapors.

In another embodiment, the signal modulation from said sensor overcomes difficulties with baseline drift and re-zeroing of said sensor thereby facilitating determination of the magnitude of the response from the stream of temporal data.

In another embodiment, detection of said one or more vapors in said detector provides for sample concentration and sample injection of said one or more vapors, including a modulation of signal data resulting therefrom.

In another embodiment, modulation of signal data provides for continuous, unattended monitoring applications.

BRIEF DESCRIPTION OF THE DRAWINGS

A more complete appreciation of the invention will be readily obtained by reference to the following description of the accompanying drawing in which like numerals in different figures represent the same structures or elements.

DETAILED DESCRIPTION OF THE INVENTION

Figure 1:
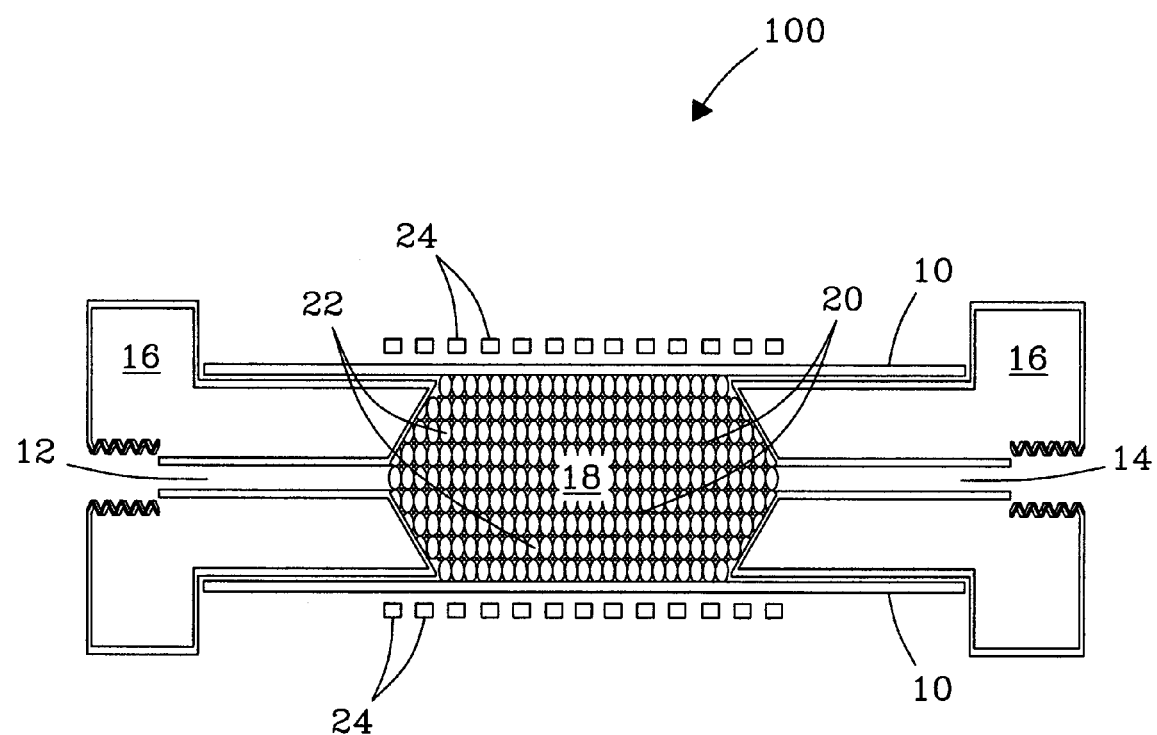
FIG. 1 is a cross-sectional view of a preconcentrator apparatus 100 according to one embodiment of the invention.

The present invention relates generally to a method and apparatus for concentrating vapors for analysis. The term "vapor" as used herein refers to a substance in a gaseous state. Vapors include, but are not limited to, e.g., inorganic vapors and organic vapors. In one embodiment, the apparatus, is a preconcentrator wherein the addition of the preconcentrator prior to real-time chemical sensor measurement of vapors provides a means to automatically sample ambient gas thereby improving measurement sensitivity. The term "Sensitivity" as used herein is a measure of the amount of signal obtained for a given vapor concentration, and is closely related to detection limit, the lowest concentration that can be detected with a signal that is distinguishable from the noise. The term "Selectivity" as used herein refers to the ability to distinguish one vapor from another in the one or more vapors or analytes to be measured.

The apparatus of this invention comprises a conduit having at least one inlet and one outlet for flowing one or more vapors in a gaseous volume therethrough, said conduit containing a sorbent for concentrating vapors from said gaseous volume by sorption, wherein said sorbent is operatively disposed within a metal foam. In one aspect of the apparatus, the conduit is a tube containing a core of metal foam with solid sorbent dispersed within the metal foam. A means is provided to flow the gas being sampled through the tube, collecting vapors on the sorbent by sorption. A means is provided to heat the tube to desorb the vapors, which under a flowing condition, exit the preconcentrator where they are detected or analyzed by a detector or instrument. The inlet and outlet can be interchangeable, for example, if the flow during desorption is in the opposite direction as the flow during collection, as is recognized in the art. The metal foam improves the heating of the sorbent during the desorption process by providing a material which provides a path with high thermal conductivity thoughout the entire sorbent bed.

When large gaseous volumes are to be processed to capture their vapors, a sufficiently high cross-sectional area of the preconcentrator is desirable to facilitate the flow. In this case, there is a significant distance from the periphery where the preconcentrator tube is heated to the center of the core of the preconcentrator. Using metal foam as part of the core improves the thermal conductivity across this distance from the periphery to the core in a configuration that enables large flow rates to be used while collecting vapors from the sample.

Rapid thermal conduction throughout the sorbent (bed) also minimizes the potential for localized overheating of sorbent that might result in decomposition and degradation of the sorbent.

In one aspect of the method, a small volume of solid sorbent collects vapors from a large gas sample (e.g., at a given flow rate for a fixed period of time) and then releases the vapors into a small gas volume during thermal desorption. This process results in a concentrated chemical pulse that generates a peak in the detector response. The initiation of heating defines when analytes are delivered to a measurement system. Signal modulation further overcomes difficulties with baseline drift and sensor re-zeroing and facilitates automated feature extraction, i.e., determining the magnitude of the response from the temporal data stream.

Heating can be very fast to desorb vapors as rapidly as possible, providing a concentrated chemical pulse with the shortest duration and highest chemical concentration. Alternatively, the heating may be less rapid, at a controlled rate of heating, to provide programmed thermal desorption of vapors from the sorbent, such that individual vapors are released at characteristic temperatures (or equivalently, characteristic times during a thermal ramp) and mixtures of vapors are separated or partially separated.

The method and apparatus find application in various functions including, but not limited to, e.g., sampling, preconcentration, sample injection, preseparation, and signal modulation. Such features are particularly useful for continuous monitoring applications with portable or unattended devices.

The preconcentrator of the invention will now be described further in reference to FIG. 1.

Figure 2:
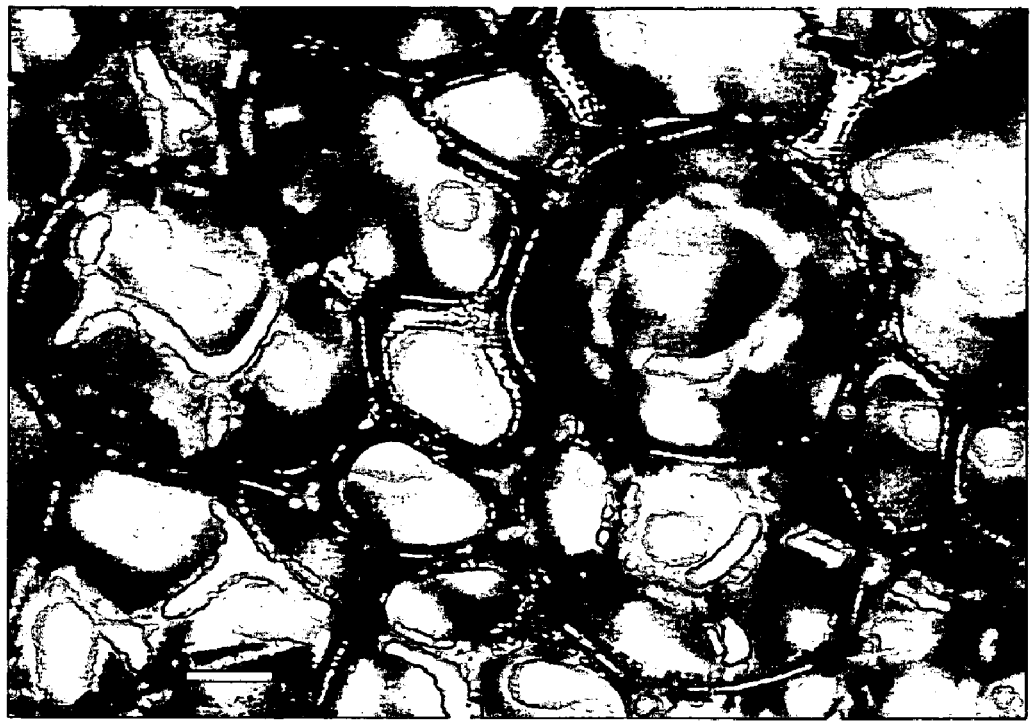
FIG. 2 is a photomicrograph that illustrates the porous structure of a metal foam, where the pore size averages 380 microns across, according to an embodiment of the invention.

FIG. 1 illustrates a cross-sectional view of a preconcentrator 100 of a benchscale design for concentrating vapors for analysis, according to one embodiment of the invention. Preconcentrator 100 comprises a conduit 10 enclosed and configured for flowing gases therethrough, e.g., via an inlet 12 and an outlet 14. Conduit 10 can be comprised of various materials, including, but not limited to, e.g., polymers, metals, glass, ceramics, or combinations thereof. No limitations are intended. In one embodiment, conduit 10 is composed of a polymer, e.g., polytetrafluoroethylene, also known as Teflon® (DuPont, Wilmington, Del., USA), with machined (e.g., Teflon) inserts 16. Conduit 10 includes a core 18 (bed) comprised of metal foam 20 with a sorbent 22 dispersed therein. Wire mesh screens (not shown) at each end of the metal foam keep the sorbent 22 within the foam 20. Inserts 16 are positioned to hold the wire mesh screens, metal foam 20, and sorbent 22 together within core 18. In addition, inserts 16 provide a means to connect inlet 12 and outlet 14 to additional devices or systems, for example to a detector. Metal foam 20 of core 18 is porous (~95% air), having a mean pore diameter of, e.g., 380 microns, but is not limited. In one embodiment, core 18 comprises a cylinder of nickel foam 20 packed with solid sorbent 22. FIG. 2 illustrates the pore structure of metal foam 20.

Metal foam 20 of core 18 facilitates thermal conductivity and temperature uniformity throughout core 18 of preconcentrator 100 during heating. The architecture of preconcentrator 100 provides rapid transfer of heat from the outer periphery of conduit 10 to the center of core 18. Metal foam 20 of core 18 further prevents agglomeration of sorbent 22 particles into a single solid mass; metal foam 20 keeps sorbent 22 particles dispersed therein.

In one embodiment, core 18 has dimensions approximately 12.7 mm long by 4.8 mm diameter, consisting of two metal foam cylinders 4.8 mm in diameter cut from a sheet supplied at 6.35 mm thick, but is not limited thereto. Core 18 comprises metal foam 20, solid sorbent 22 dispersed within metal foam 20, two wire mesh screens (e.g., Inconel 600 wire mesh disks with 120 mesh size, 0.094 mm from Tri Screen Inc, Claremont, Calif., USA), and two opposing Teflon® inserts 16 inserted into conduit 20. In the instant embodiment, conduit 20 is a 58 mm length of Teflon® 8-gauge shrink tube (e.g., Voltrex™ tubing, SPC Technology, Chicago, Ill., USA). Teflon® tubing is thermally shrunk to seal connections between the tube 20 and inserts 16. An additional layer of shrink tubing is used to secure a heater 24 (e.g., a model HK5573R5.1 Kapton foil heater, MINCO, Minneapolis, Minn., USA) and a thermocouple (e.g., a model #5TC-TT-K-36-36-SMP-M, Type-K, thermocouple, OMEGA Engineering, Inc., Stamford, Conn., USA) around the outer diameter of conduit 10. With its Teflon® inserts 16 and Teflon® conduit 10, metal foam 20 of core 18 containing sorbent 22 is the most thermally conductive component of preconcentrator 100.

Sorbents

Choice of sorbent is not limited and depends in part on vapors to be concentrated and the desorption temperatures desired, as will be understood and selected by those of skill in the art. No limitations are intended. Sorbents include, but are not limited to, e.g., resins (e.g., Tenax-TA™, Carbotrap, Carboxen, Carbosieve, glass beads), polymers, molecular sieves, activated carbons, carbon nanotubes, ceramics, aluminas, silicas, silica gels, dessicants, or the like, or combinations thereof. Sorbent particles may be of any size provided that flow of vapors through preconcentrator 100 is not restricted and particles can be dispersed in the metal foam 20 of core 18. Mesh size is selected in the range from about 30 (200 microns) to about 400 (37 microns), but is not limited thereto.

In one exemplary embodiment, sorbent is composed of 2,6-diphenylene-oxide, a porous polymer also known as Tenax-TA™ available commercially (Scientific Instrument Services, Ringoes, N.J., USA). Tenax-TA™ is preferably of a 60/80 mesh size, with a grain size diameter of from about 170 microns to about 250 microns. In exemplary tests described further herein, core 18 was loaded with 25 mg Tenax-TA™ but is not limited thereto. For example, the approach is extensible to other sorbents. For example, core 18 has been packed with Carboxen-569™ sorbent (Supelco, Inc., Bellefonte, Pa., USA) in the metal foam 20, crushed and sieved to a 60/80 mesh size from an as-received 20/40 mesh. Thus, no limitations are intended.

Operation of the Preconcentrator

During operation, a small volume of sorbent collects vapors from a large gas sample (e.g., at a given flow rate for a fixed period of time) and then releases the vapors into a small gas volume during thermal desorption. Desorption provides a concentrated chemical pulse that generates a response (signal) in a detector or instrument coupled thereto. The heating may be rapid, generating a brief concentrated chemical pulse containing the adsorbed vapors, or it may be less rapid, wherein the vapors are desorbed in a programmed thermal desorption leading to separated or partially separated vapors.

In either approach, using a highly porous metal foam to contain the sorbent and improve thermal conductivity throughout the sorbent bed is advantageous.

Controlled Thermal Desorption via use of Heaters

Because control of the thermal desorption of vapors is desired from sorbent 22 present in core 18, an effective means of heating the entire core 18 of conduit 10 is desired. Non-uniform heating and/or temperature of sorbent 22 can result in nonuniform release of vapors during the thermal desorption process, leading to broader peaks. Preconcentrator 100 is thus preferably coupled to a heater 24. Heaters include, but are not limited to, e.g., resistive heaters, band heaters, strip heaters, radiant heaters, multi-cell heaters, multi-coil heaters, polymer heaters, rapid response heaters, heat-exchangers, tape heaters, cable heaters, tubular heaters, cast-in heaters, cartridge heaters, ceramic fiber heaters, or the like. No limitations are intended. In one embodiment (described in reference to FIG. 1), heater 24 is a resistive heater 24 (e.g., a model HK5573R5.1 Kapton foil heater, MINCO, Minneapolis, Minn., USA) positioned (e.g., wrapped) around conduit 10 for desorbing vapors from sorbent 22 of core 18 of preconcentrator 100. Resistive heater 24, having RTD properties, may simultaneously function as a temperature sensor for monitoring and providing feedback control of the temperature Preconcentrator 100 is further optionally configured with one or more thermocouples for measuring and monitoring temperature during thermal calibration and desorption experiments. Heater 24 provides for thermal desorption of vapors from preconcentrator 100. Heater 24 and a means of monitoring the temperature and adjusting the power to heater 24 provide a means for controlled programmed thermal desorption of vapors from preconcentrator 100.

Figure 3:
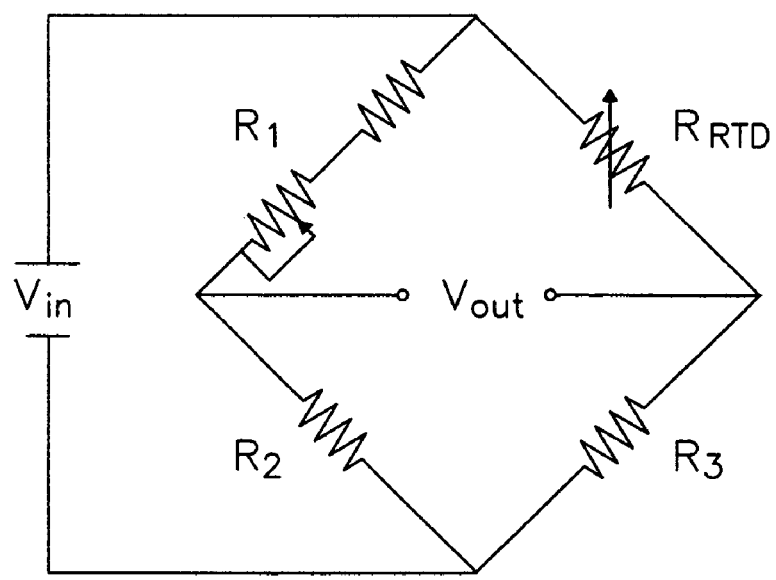
FIG. 3 illustrates a Wheatstone bridge used for feedback control of thermal ramp rate and temperature measurement, according to an embodiment of the invention.

In one exemplary embodiment, a simplified Wheatstone bridge circuit, illustrated in FIG. 3, is used to monitor and control temperature of heater 24. In the instant embodiment, a resistive heater (heater 24 in FIG. 1), having resistance temperature detector (RTD) properties, serves as one leg of the bridge, such that the bridge balance voltage is directly proportional to the RTD resistance and thus temperature. The bridge is initially balanced so that the bridge balance voltage is zero at room temperature. Due to its resistance temperature detector (RTD) properties, heater 24 provides rapid heater temperature feedback.

A custom LabVIEW™ software program and a multifunction data acquisition card (e.g., a model 6030E PCI data acquisition card, National Instruments, Austin Tex.) is used to control the thermal ramp. An input voltage, $V_{in}$, is supplied from a digital-to-analog converter (DAC) to raise temperature of heater 24. Bridge balance voltage, $V_{out}$, is measured using an analog-to-digital converter (ADC). Input voltage is slewed programmatically to obtain a desired ramp rate and end point while monitoring the bridge balance voltage at, e.g., a 35 Hz update rate. Temperature of preconcentrator 100 is ramped at controllable rates under software control by monitoring temperature and adjusting voltage to heater 24 at an update rate of, e.g., 35 Hz. Increasing the input voltage increases current through heater 24, increasing the temperature, and changing its resistance. The change in resistance leads to a change in bridge balance voltage which is monitored and fed into a temperature control algorithm in order to determine a subsequent input voltage. Calibration is provided by independently monitoring temperature with a thermocouple, which calibration is used with the bridge balance voltage in a control algorithm. With this technique, preconcentrator 100 can be ramped from, e.g., room temperature to 170° C. in a linear fashion in 30 seconds or longer. No limitations are intended. Preconcentrator 100 can be designed and controlled for faster or slower linear thermal ramps, or to ramp the temperature in controlled nonlinear ways.

Control schemes employing separate heater and temperature sensor elements can suffer from thermal offset and overshoot. To minimize these problems, temperature control must be sufficiently damped. An overly damped control approach, however, cannot provide sufficiently fast response needed to precisely control large thermal ramps because, e.g., ΔT can be a range of up to about 200° C. Use of heater 24 as a temperature sensor for preconcentrator 100 provides fast temperature response to accurately control and provide fast thermal ramping. In addition, rapid heater RTD feedback facilitates fast thermal ramping with minimal thermal offset or overshoot.

Thermal Ramps

Thermal ramp designs are not limited, as will be understood by those of skill in the art. In one exemplary approach, thermal ramp is started at a preset ramp rate, ranging from about 0.8° C./sec to about 15° C./sec, to a first maximum preset temperature. The maximum temperature is selected to be sufficient to desorb all the vapors while not being so high that thermally induced degradation of the sorbent medium occurs. At the top of the thermal ramp, temperature is held for a preselected period to allow test vapors to fully desorb. At the end of the ramp hold period and the vapor desorption, preconcentrator 100 is allowed to thermally cool back to ambient temperature in preparation for the next cycle. No limitations are intended.

Linear Temperature Ramping for Temporal Separation

Effect of thermal ramp rate on vapor mixture resolution using a practical preconcentrator 100 design operated at multiple thermal ramp rates is described herein. Temporal separation of desorbing vapors at varying linear rates of temperature increase has been examined using a selected metric for resolution to determine if the rate of thermal desorption influences the resolution achieved in a practical preconcentrator configuration. Preconcentrator 100 provides good thermal uniformity throughout the packed bed of sorbent in core 18. Peak resolution in the analysis of mixtures can be improved by decreasing the thermal ramp rate compared to heating of preconcentrator 100 as rapidly as possible.

Peak Resolution

The term "Peak Resolution" as used herein refers to the amount of peak overlap for pairs of peaks or the ability quantify resolution. An empirical formula for determining the peak resolution factor, $R_s$, a measure of peak overlap, and thus resolution, is calculated as a ratio containing the difference in position of peak maxima in the numerator and the sum of the peak widths in the denominator, by equation [1]:

$$R_s = 1.18(t_r1 - t_r2)/(pwhh1 + pwhh2) \quad [1]$$

where $t_r$ values are peak retention times for any two peaks. The value for $R_s$ depends on the measure of peak width being used. Here, peak width is expressed in terms of peak width at half height (pwhh), but is not limited thereto. Values obtained provide an indication of peak resolution, where higher values indicate less overlap between two peaks. For Gaussian peaks of equal height in chromatography, a value greater than 0.5 is required to observe separate peak maxima; a value greater than 1.5 indicates a baseline resolution. As values become larger, further baseline increases between peaks are observed.

Sensors

Choice of sensors and/or detectors for quantifying and detecting vapors desorbed from preconcentrator 100 is not limited. Selection of sensors and detectors depends on desired sensitivity, selectivity, and/or vapors to be measured, as will be understood by those of skill in the art. Sensors and detectors include, but are not limited to, e.g., multivariate detectors, chemometric detectors, sensor arrays, ion mobility spectrometers, mass-spectrometers, gas chromatographys, gas chromatography detectors, chemical sensors, or the like.

Figure 4:
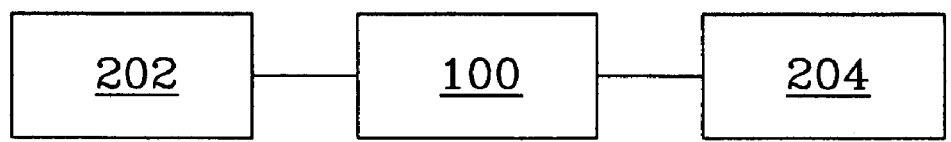
FIG. 4 illustrates a system for generating vapors and detecting vapors in conjunction with a preconcentrator, according to another embodiment of the invention.

In one exemplary configuration, preconcentrator 100 is connected to a flow cell containing a single polymer-coated microsensor as a detector, e.g., a Flexural Plate Wave (FPW) Sensor 204, to measure desorption of vapors from preconcentrator 100. The experimental apparatus is shown in FIG. 4. A vapor blending system, VBS, 202, is used to prepare diluted vapor samples and samples containing mixtures of vapors and deliver them to preconcentrator 100. FPW sensor 204 is located downstream from preconcentrator 100.

FPW sensors mounted on separate alumina headers and oscillator circuits are available commercially (Berkeley Micro Instruments, Berkeley, Calif., USA). In the instant configuration, the FPW sensor has a resonant frequency of 8 MHz, with etch pits 6 mm long and 0.5 mm wide, but is not limited thereto. The alumina headers contain a window over which the dies are mounted, with the FPW etch pit facing away from the header and the metallized side exposed through the bottom of the header, where electrical connections are made. Prior to coating, FPW sensor 204 is rinsed with dichloromethane and air dried, then cleaned with a UV-ozone device (e.g., a Model 342 UV-ozone Cleaner, Jelight Inc., Irvine, Calif., USA) or cleaning method. FPW sensor 204 is spray-coated with a polydimethylsiloxane (PDMS) polymer to a frequency shift of 100 kHz. The film is examined after being applied by optical microscopy using a microscope (e.g., a Nikon Optiphot-M, OPTOTEK, Silicon Valley, Calif., USA) in conjunction with Nomarski reflected light differential interference contrast. In the instant embodiment, (coated) FPW sensor 204 sensor is mounted in an aluminum flow cell (not shown) with a gas inlet and gas outlet, with the entire flow cell plus associated electronics maintained at 25° C. The inlet and outlet channels of the flow cell are placed at each end of the sensor etch pit, and the etch pit channel is used for flow over the sensing film thereby minimizing dead volumes. The flow cell is connected by ⅟₁₆" Teflon tubing directly to outlet 16 of preconcentrator 100. In one exemplary approach, frequency data from the FPW sensor oscillator are recorded every two seconds using a High Performance Universal Counter (e.g., a model 53131A universal counter, Hewlett-Packard, Palo Alto, Calif., USA) with a medium stability timebase, and data are transferred to a computer (e.g., a Macintosh computer, Apple Computers, Cupertino, Calif., USA) via a IEEE-488 bus. Data are collected with, e.g., Labview™ software (National Instruments, Austin, Tex., USA)

For some experiments, another frequency data collection method was used. Frequency of FPW sensor 204 is measured, e.g., using a counter (e.g., a model 6602 PCI counter configured with an 8 channel, 32-bit counter PCI card having an internal 80 MHz timebase, National Instruments, Austin, Tex., USA). In exemplary tests, two counters are used. A first counter (Counter 0) counts a user-specified number of FPW frequency cycles, and a second counter (Counter 1) times how long it takes to count a specified number of cycles, using the internal timebase as a clock. Measured frequency of the FPW signal represents the user-specified number of cycles counted divided by the elapsed time required to count them. The elapsed time is measured as the number of cycles counted on the second counter divided by 80,000,000. The frequency measurements are transferred directly to the computer CPU (e.g., via a 133 MHz PCI bus). Labview™ software reads, displays, and logs frequency data.

Use of Preconcentrator for Partial Separations

The operation of preconcentrator 100 for partial separation of vapors is fundamentally different from use of preconcentrator 100 for preconcentration and injection of vapors. In the latter case, desorption from preconcentrator 100 is preferably fast and sharp to obtain the tallest detection peaks possible and to minimize band broadening from injection, e.g., when coupled with a chromatographic instrument or step. When preseparations are desired however, vapors are preferably desorbed in a way that spreads them out over time. Accordingly, the influence of thermal ramp rate on partial separation of vapor mixtures is a factor in the configuration and method of use selected for preconcentrator 100.

For example, in one exemplary embodiment of an advanced instrument for vapor detection, preconcentrator 100 can be coupled to a multivariate detector. In the instant embodiment, use of a multivariate detector such as a sensor array in combination with preconcentrator 100 providing at least partial temporal vapor separation creates a system that can take advantage of advanced chemometric methods for better chemical information extraction. Addition of preconcentrator 100 to a sensor array system, and processing the data with advanced chemometrics methods can overcome some of the limitations of an array alone, even if preseparation achieved with preconcentrator 100 does not provide baseline resolution (i.e., resolution values of 1.5 or better). Mathematically, such an approach represents a second-order system one obtains two vectors of data per sample. By contrast, a sensor array alone is a first order measurement that provides only one vector of data per sample. Additional information provided by a second-order system configuration can provide improved selectivity and the potential to quantify vapors and/or analytes in the presence of unknown interferences.

The use of a preconcentrator incorporating metal foam is advantageous for development of a second order system because it can provide a better preseparatoin than an equivalent preconcentrator lacking the metal foam. The better preseparation in front of the multivariate detector, which results from better temperature uniformity of the bed during controlled thermal desorption, provides better data for processing by second order chemometric methods.

In addition, use of upfront separation in conjunction with a multivariate detector allows use of multivariate curve resolution techniques that can mathematically resolve overlapping peaks, even at low resolutions. Such methods can be used to quantify analytes in mixtures and to obtain pure component spectra, even at resolutions below 0.5 where separate peak maxima are not seen. Hence, there is great value in obtaining even partial temporal resolution of vapor mixtures.

The ability to obtain pure component patterns from multivariate curve resolution techniques further enables use of new classification techniques. For example, pure component vapor patterns can be used in a classification method that transforms such vapor patterns into descriptors of the vapor solubility properties for sorbed vapors sorbed as a mass, as a volume, and for mixtures. Thus, using a preseparator/array instrument and multivariate curve resolution, pure component patterns can be extracted which can then be classified.

The following examples are intended to promote a further understanding of the present invention. Example 1 describes results for preconcentrators with and without metal foam. Example 2 describes vapor mixture desorption experiments in conjunction with preconcentrator 100 where vapors are desorbed at varying thermal ramp rates leading to improved mixture resolution. Example 3 describes results for vapor separation tests using preconcentrator 100 for a tertiary mixture of MEK-TOL-DMMP vapors, with varying DMMP concentrations

EXAMPLE 1

Preconcentrators with and without Metal Foam Core

Example 1 describes thermal characteristics of a preconcentrator containing metal foam 20 in core 18 of preconcentrator 100 in comparison to one lacking metal foam, which demonstrates that the metal foam improves thermal conductivity and thermal uniformity in the sorbent bed. In addition, it has been observed in vapor desorption tests that preconcentrators without metal foam lead to broader more overlapped peaks from vapor mixtures. Thus the metal foam also provides narrower better resolved vapor desorption peaks.

Figure 5A:
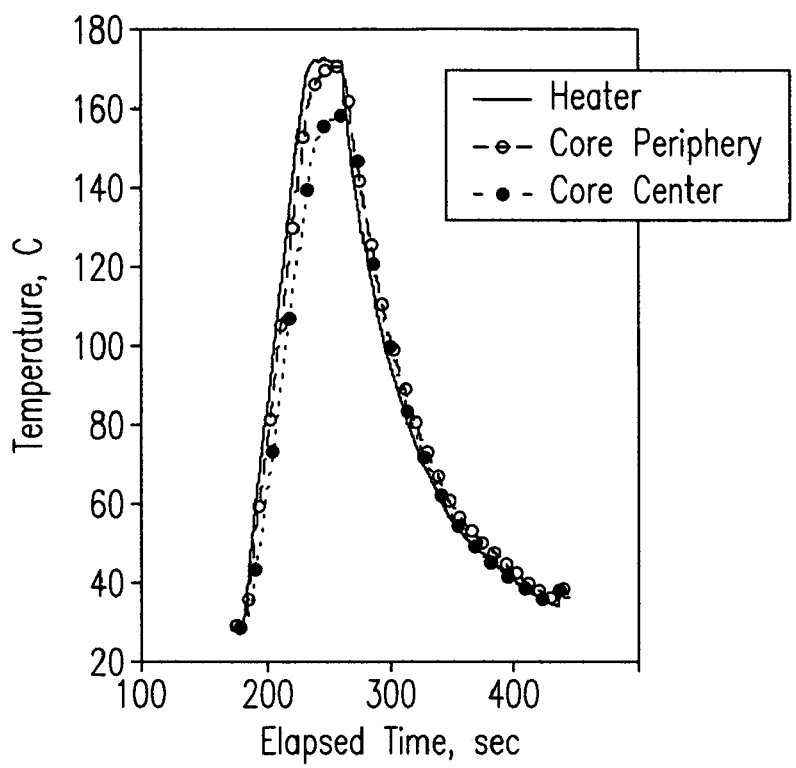
FIGS. 5a-5b present thermal profiles of a preconcentrator without and with a metal foam core.
Figure 5B:
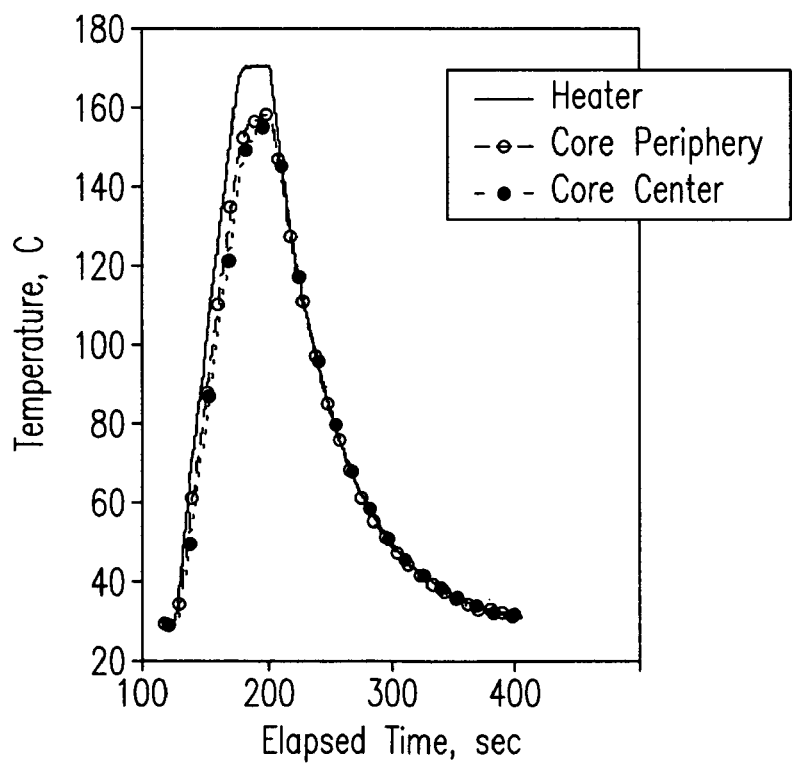

Experimental. Preconcentrator 100 with core 18 of metal foam 20 was packed with ~25 mg of 60/80 mesh Tenax-TA™ sorbent (Supelco, St. Louis, Mo., USA) 22. Metal foam 20 used was a porous nickel foam (e.g., Ampormat 200 series, Astro Met Inc., Cincinnati, Ohio, USA) having a pore density of about 60 pores per inch in sheets. Preconcentrators prepared without metal foam 20 in the core were also prepared for comparison purposes. The same quantity (~25 mg) of sorbent (e.g., Tenax®) 22 was packed into the preconcentrator lacking metal foam as was packed into the preconcentrator that contained metal foam. Teflon® adapters in the preconcentrators lacking metal foam were inserted further into conduit 10 as the volume of Tenax® sorbent 22 particles alone was slightly lower than that observed for core 18 of preconcentrator 100 including metal foam 20. Thermocouples (e.g., model #5TC-TT-K-36-36-SMP-M, Type-K thermocouples, OMEGA Engineering, Inc., Stamford, Conn., USA) were inserted into the preconcentrators to measure temperatures at the center and periphery of the core 18 of each. Thermocouples had a head diameter of about 250 microns, comparing with Tenax® particles of from about 170 to about 250 microns. In addition, a thermocouple was present on the outside of preconcentrator 100 conduit 20, as usual. The resistive heater 24 of preconcentrator 100 was included as a leg of a simplified Wheatstone bridge, as described hereinabove with reference to FIG. 3. Increasing the input voltage increased current through heater 24, increasing the temperature, and thus changing its resistance. The change in resistance led to a change in bridge balance voltage which was monitored and fed into a temperature control algorithm to determine a subsequent input voltage. Preconcentrator 100 temperatures were ramped at controllable rates under software control by monitoring temperature and adjusting voltage of heater 24 at an update rate of 35 Hz. FIGS. 5a and 5b compare thermal characteristics of core 18 of preconcentrator 100 with and without metal foam 20. Results are shown for a 60 sec temperature ramp.

Results. As illustrated in FIGS. 5a and 5b, significant and observable temperature differences are noted between the center and periphery of the cores of preconcentrators without metal foam as preconcentrator 100 heats up. As illustrated in FIG. 5a, in the absence of metal foam 20, as the periphery of core 18 heats to the heater temperature, over 10 degrees difference exists in temperature observed across the radius of core 18, e.g., between the periphery and center of core 18. As illustrated in FIG. 5b, when metal foam 20 is present in core 18, temperature at the center of core 18 closely tracks temperature observed at the periphery of core 18. Core 18 of preconcentrator 100 with metal foam thus maintains a more uniform temperature across its radius. Thus, the results show that the metal foam improves the heating throughout the sorbent bed of the preconcentrator and provides more uniform sorbent bed temperatures.

Figure 6A:
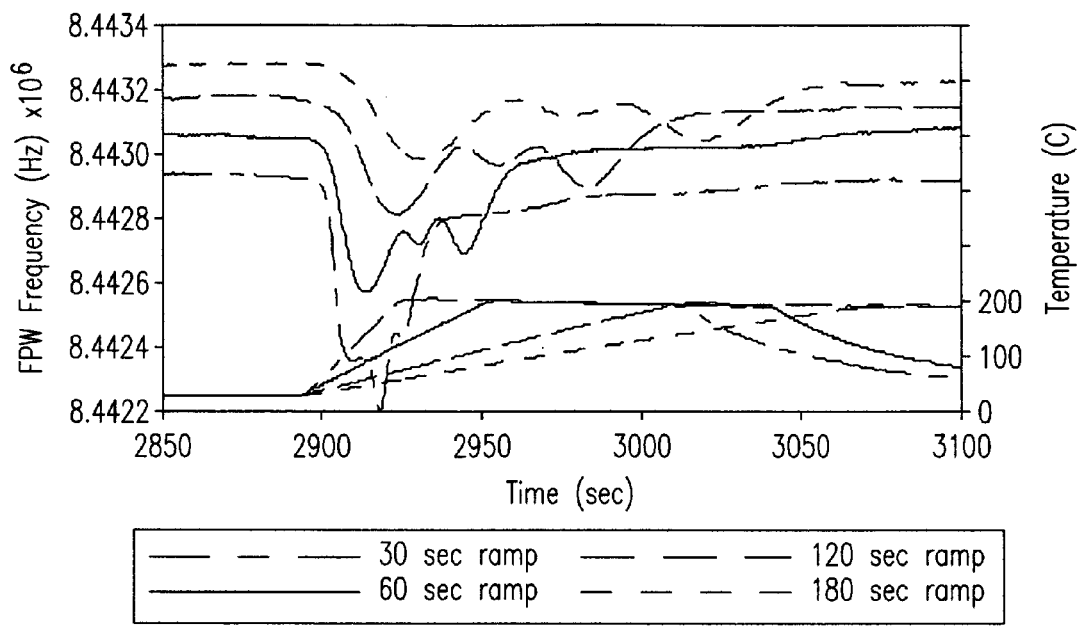
FIGS. 6a-6b present vapor mixture desorption results at varying thermal ramp rates for preconcentrators with and without metal foam.
Figure 6B:
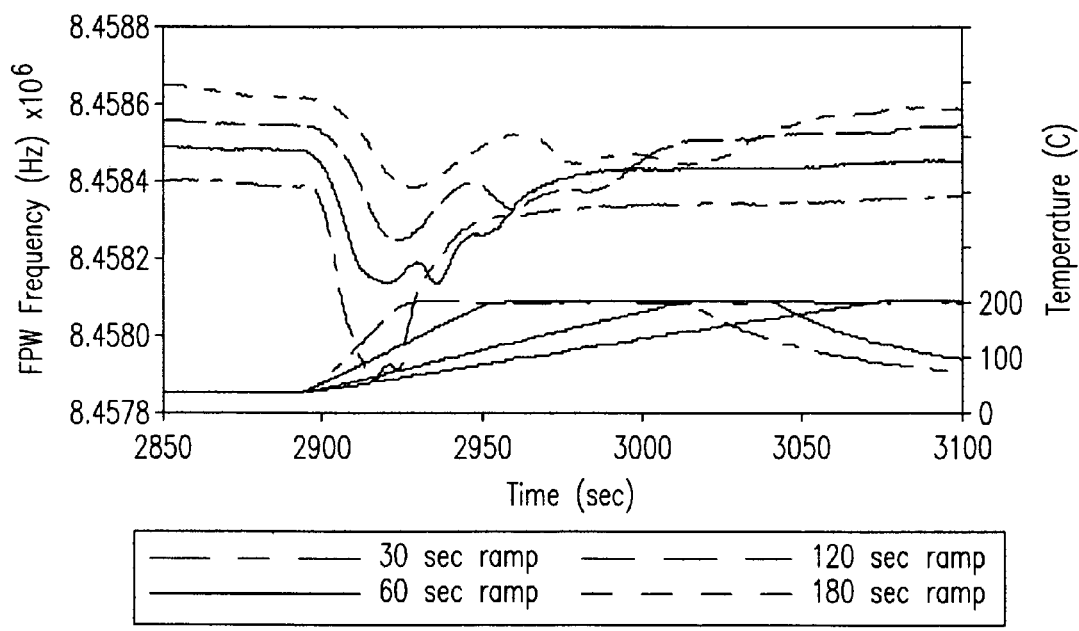
Figure 7:
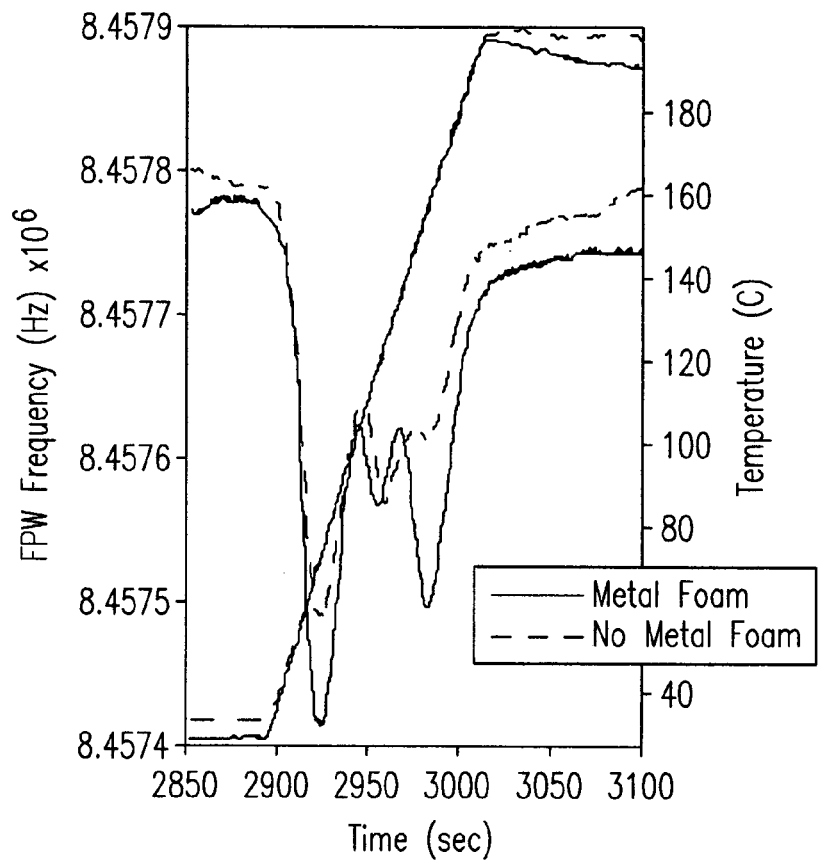
FIG. 7 compares mixture desorption profiles at 120 sec ramp time for preconcentrators with and without metal foam.

Preconcentrators with and without metal foam were also used to collect vapor mixtures and desorb them to a sensor. In the absence of metal foam 20, preconcentrators yielded broader, more overlapped peaks during desorption of vapor mixtures. Preconcentrators 100 with metal foam provided narrower peaks and visibly better peak resolution. Results are shown in FIGS. 6a, 6b, and 7. Preconcentrators with and without metal foam were prepared as described above, each with 25 mg of Tenax® sorbent 22. Preconcentrator 100 was placed in series between a vapor generator 202 (e.g., VBS system) and a single FPW sensor 204 acting as detector in a system 200 described previously in reference to FIG. 4. Ternary mixtures of vapors were generated consisting of 2240 mg/m$^3$ methyl ethyl ketone (MEK), 220 mg/m$^3$ toluene (TOL), and 82 mg/m$^3$ dimethyl methylphosphonate (DMMP), obtained from Aldrich (St. Louis, Mo., USA). Vapors used are representative of vapors having different functionalities and volatility in order to demonstrate varying desorption rates from preconcentrator 100. Flow rates during the experiments were 25 mL/min and the preconcentrators were heated to 200° C. during the desorption process. FIGS. 6a and 6b show the desorption of ternary mixtures at the various thermal ramp rates. By comparing the desorption peaks observed in FIG. 6a for the preconcentrator containing metal foam with those in FIG. 6b for the preconcentrator lacking metal foam, it is seen the peaks are better resolved using metal foam. FIG. 7 compares results for preconcentrators with and without metal foam in one figure, selecting the 120 second ramp time as an example. It is clearly seen that with metal foam the peaks are taller and more symmetrical and better resolved than seen without metal foam.

EXAMPLE 2

Vapor Separation of a Tertiary Mixture as a function of Heating Ramp Rate

Example 2 describes test results using preconcentrator 100 containing metal foam for vapor separation of a tertiary mixture of MEK-TOL-DMMP vapors. Peak separation and resolution were demonstrated and measured by varying the controlled thermal ramp rate of preconcentrator 100 as described herein.

Figure 8:
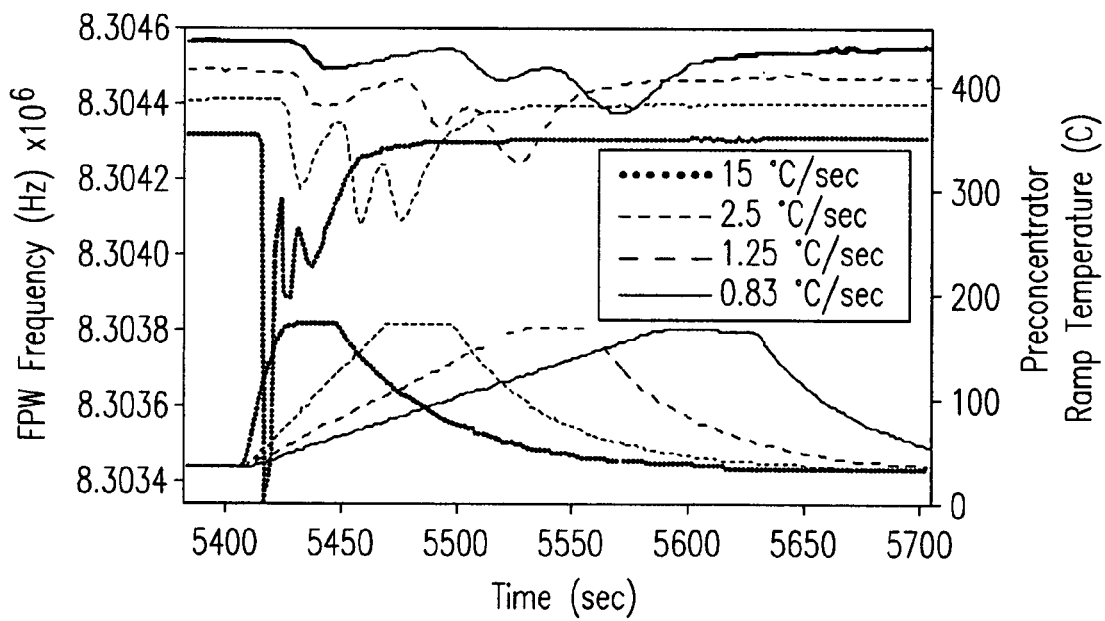
FIG. 8 presents response profiles for a three-vapor mixture as a function of preconcentrator heating ramp rate.
Figure 9:
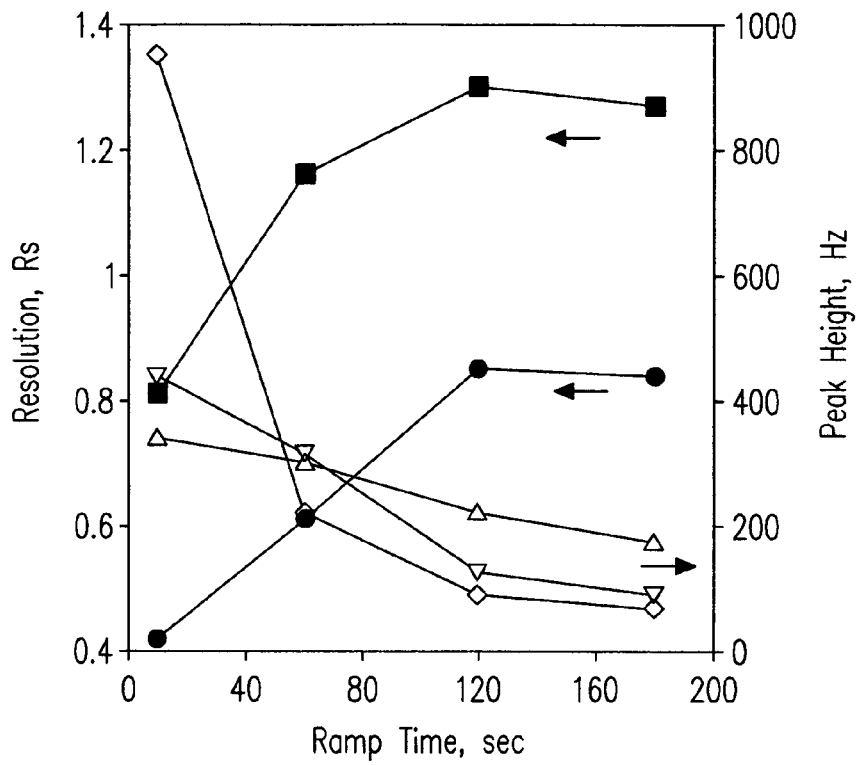
FIG. 9 shows peak resolution data as a function of temperature ramp time, according to one embodiment of the process of the invention.

Experimental. Preconcentrator 100 was placed in series between a vapor generator 202 (e.g., VBS system) and a single FPW sensor 204 acting as detector as described previously. Ternary mixtures of vapors were generated consisting of methyl ethyl ketone (MEK), toluene (TOL), and dimethyl methylphosphonate (DMMP), obtained from Aldrich (St. Louis, Mo., USA), representing vapors having different functionalities and volatility in order to demonstrate varying desorption rates from preconcentrator 100. Vapor concentrations of the tertiary mixture of vapors were 2230 mg/m$^3$ MEK, 220 mg/m³ TOL, and 110 mg/m³ DMMP, respectively. A two minute vapor collection period was employed. Vapors desorbed from preconcentrator 100 were detected using a single polymer-coated FPW sensor 204 in a low dead volume flow cell. Four thermal ramp rates were using ranging from about 15° C./sec (10 sec ramp) to about 0.83° C./sec (180 sec ramp), i.e., at 10 sec., 60 sec., 120 sec., and 180 sec., respectively. Maximum ramp temperature was ~170° C. Flow rate of nitrogen sweep gas was 100 sccm. FIG. 8 shows the effect of thermal ramp rate on peak shape and separation provided by preconcentrator 100 as a function of heating ramp rate. Response profiles are shown for the three-vapor mixture. Thermal profiles for the four thermal ramp rates are shown in the lower traces (referenced to the right y-axis). The thermal ramp was programmed to be linear at all four thermal ramp rates. Vapor peaks detected by FPW sensor 204 are shown in the upper traces (referenced to the left y-axis) resulting in a family of curve traces. Traces are offset for clarity. Resolution results are shown in FIG. 9. Peak resolutions were calculated according to a metric for resolution ($R_s$) described hereinabove.

Results. In FIG. 8, actual thermal ramps are linear for the 60, 120, and 180 second ramps. Vapors are released in the order of MEK, TOL, and DMMP. As thermal ramp rate becomes slower, positions of the peak maxima shift to longer time positions and are more widely separated. At the same time, peak heights become lower as the peaks become broader. In FIG. 9, peak resolutions increase as a function of temperature ramp time up to a ramp time of 120 seconds. The left axis shows $R_s$, the peak resolutions, plotted with reference to the left y-axis where squares correspond to resolution of MEK and TOL and circles correspond to resolution between TOL and DMMP. Peak heights referenced to the right y-axis are included for comparison. The peak heights as a function of ramp time are shown as dashed lines referenced to the right y-axis, where the triangles pointing up are for DMMP, the triangles pointing down are for TOL, and the diamonds are for MEK. Resolution of the vapor mixture improves with increasing thermal ramp time up to about 120 seconds. Resolution improves even as peaks become broader. Preconcentrator 100 in combination with programmed thermal desorption can thus be used as a pre-separator in addition to its usual functions for sampling, signal modulation, and improving sensitivity. As specified in example 1, preconcentrators without metal foam result in broader peaks and less resolution of vapor mixtures, and hence are of less use as a preseparator.

EXAMPLE 3

Preconcentration of Varying Vapor Concentration in a Tertiary Mixture

Example 3 describes results from vapor separation tests using preconcentrator 100 involving tertiary mixtures of MEK-TOL-DMMP vapors at constant MEK-TOL with varying concentrations of DMMP. Tests on binary mixtures of MEK-TOL and TOL-DMMP were also conducted for comparison purposes.

Figure 10:
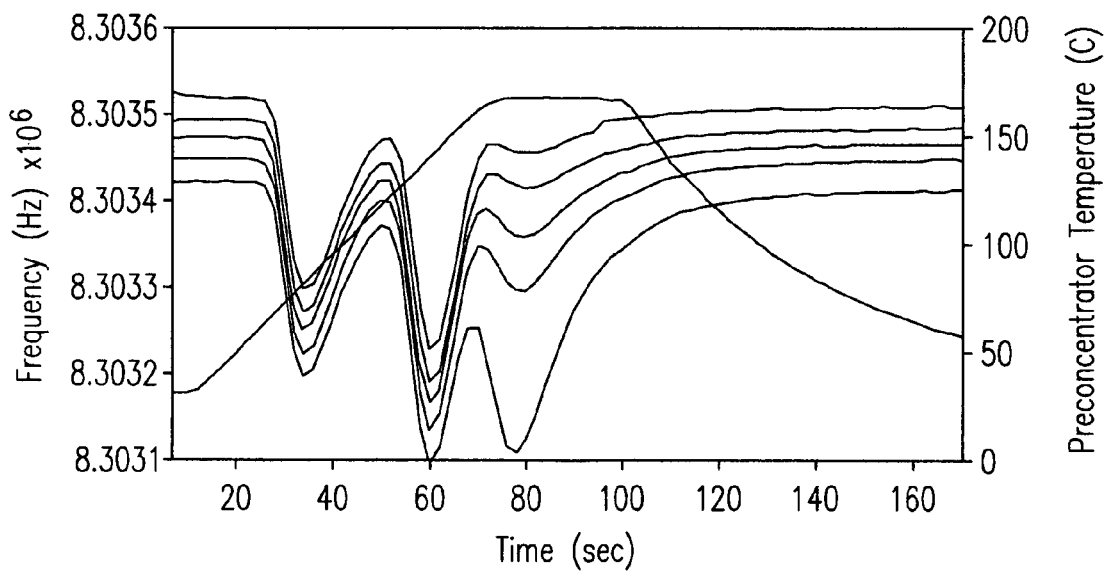
FIG. 10 presents response profiles for a tertiary vapor mixture of MEK-TOL-DMMP at constant MEK-TOL and varying DMMP.

Experimental. Ternary mixtures of vapors were generated consisting of methyl ethyl ketone (MEK), toluene (TOL), and dimethyl methylphosphonate (DMMP) as described in Example 2. Concentrations were held constant for MEK and TOL at 2230 mg/m³ and 220 mg/m³, respectively. DMMP vapor concentrations were varied, ranging from 6.9, 13.7, 27.4, 54.8, and 110 mg/m³. The MEK-TOL-DMMP vapor mixtures were preconcentrated using preconcentrator 100 as described in Example 2. FIG. 10 plots the response profiles at a single thermal ramp rate of 2.5° C./sec (60 sec ramp). Ramp temperature is overlaid, referenced on the right hand Y-axis.

Results. In FIG. 10, the effect of varying one component (DMMP) while maintaining the other components (MEK and TOL) constant is demonstrated. MEK and TOL peak shapes and separation are unaffected by changing the third component (DMMP); peak areas and peak heights for DMMP increase with increasing DMMP test concentration as expected. Results described previously in Example 2 for tests on tertiary mixtures of MEK-TOL-DMMP did not show significant differences from those in binary mixture tests of MEK-TOL and TOL-DMMP. Peak separation times between the pairs of peaks in both the binary mixture tests and tertiary mixture tests are comparable; no significant differences are observed between test results. Addition of a third component did not change the respective peak parameters for the other two components. This example demonstrates that when the preconcentrator apparatus is designed and operated to provide separations, it is possible to monitor varying concentrations of a component even in the presence of other components in the mixture.

Figure 11:
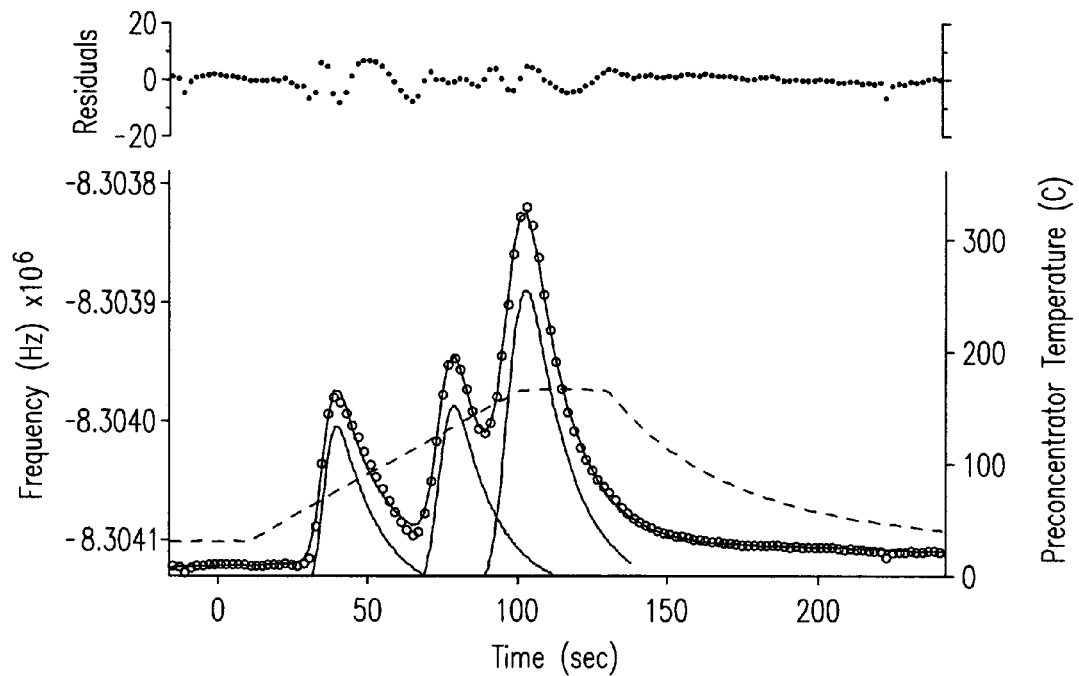
FIG. 11 is a plot of modeled peak data, using an exponentially-modified Gaussian fit, according to one embodiment of the process of the invention.
Figure 12:
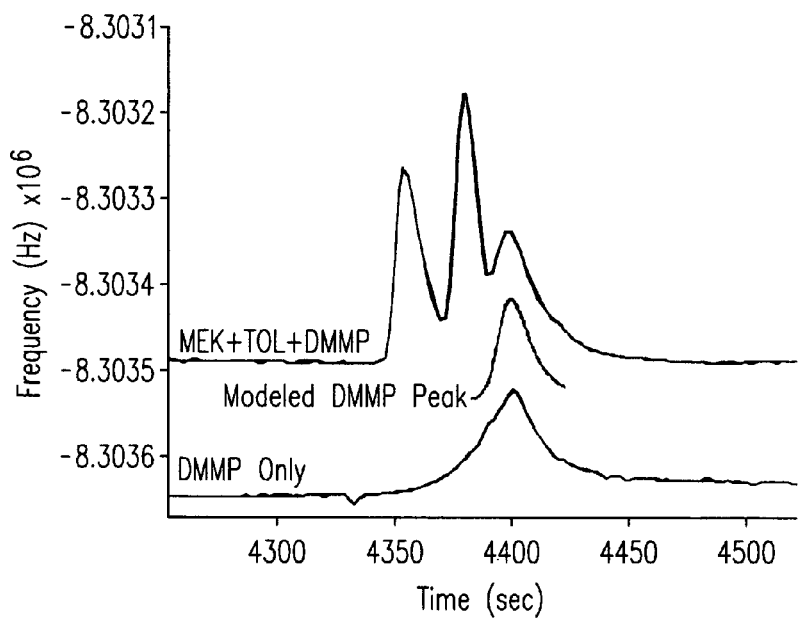
FIG. 12 compares modeled peak data from a ternary mixture compared with peak data from a single vapor.
Figure 13:
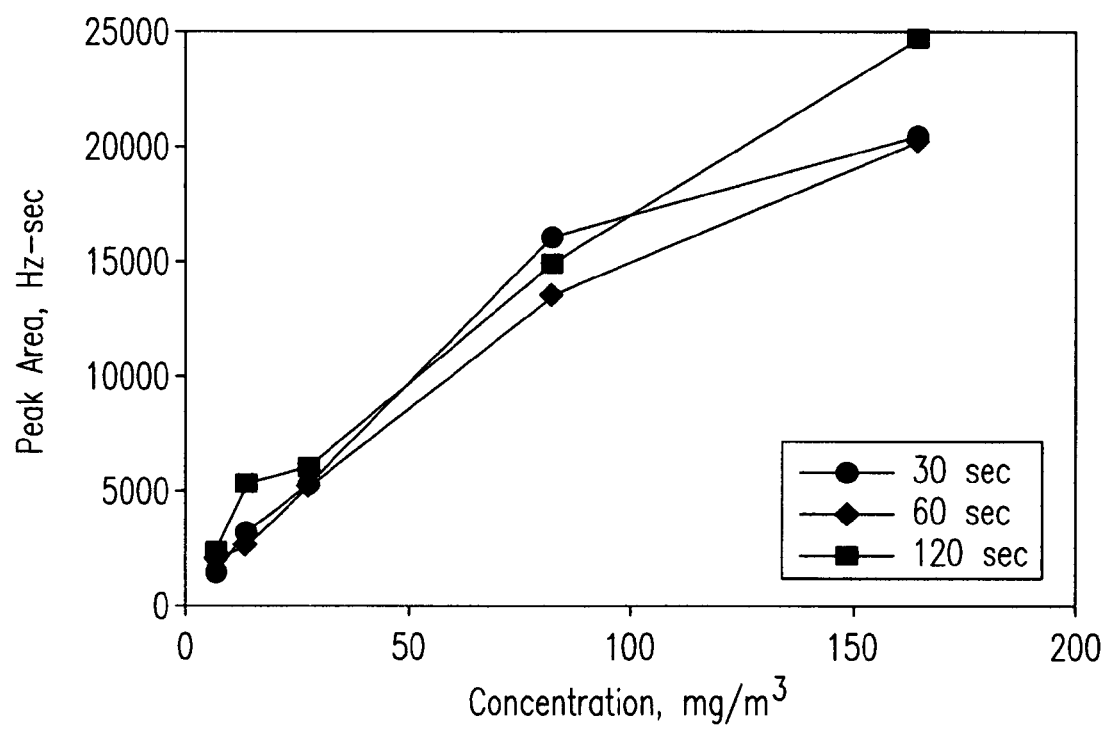
FIG. 13 compares modeled peak data using exponentially modified Gaussian model for curve fitting at varying thermal ramp times of 30, 60, and 120 seconds.

When vapors are desorbed as partially overlapping peaks, curve fitting techniques can be used to extract individual peak profiles, and hence determine the peak heights and peak areas of the individual vapors. When a univariate sensor is used, conventional curve fitting techniques known in the art can be used. FIG. 11 shows peak fitting for data collected using preconcentrator 100 containing metal foam in conjunction with FPW sensor 204 as described hereinabove. The data points are as open circles. The solid curve shows the peak fitting, and the underlying peak traces show the individually modeled peaks. An exponentially modified Gaussian peak shape was used for modeling and peak fitting. FIG. 12 shows a ternary mixture, the modeled DMMP peak from the mixture, and an experimental trace from an experiment with DMMP that is not in a vapor mixture. Peak areas for DMMP in mixtures were determined by this method in calibration experiments at multiple DMMP concentrations and various thermal ramp rates. FIG. 13 shows that similar peak areas are obtained at each concentration regardless of the thermal ramp rate. Therefore, peak areas can be used to quantify the amount of DMMP in the sample even when the sample is in a mixture, provided that one obtains sufficient preseparation.

Such curve fitting approaches improve in precision and accuracy the better the peaks in the mixture are resolved. Since the metal foam improves the peak resolution, it improves the precision and accuracy with which vapors can be quantified in mixtures when detected by a univariate detector.

If the detector is a multivariate detector, then multivariate curve resolution methods can be used to extract pure component concentration profiles. These curve fitting approaches also improve in precision and accuracy the better the peaks in the mixture are resolved. Since the metal foam improves the peak resolution, it improves the precision and accuracy with which vapors can be quantified in mixtures when detected by a multivariate detector While the preferred embodiments of the present invention have been shown and described, it will be apparent to those skilled in the art that many changes and modifications ma be made without departing from the invention in its true scope and broader aspects. The appended claims are therefore intended to cover all such changes and modifications as fall within the spirit and scope of the invention.

We claim:

1. An analytical system characterized by a preconcentrator, said preconcentrator comprising:
   a tube defining a conduit having at least one inlet and one outlet for flowing one or more vapors in a gaseous volume therethrough, said conduit filled with a metal foam core;
   said metal foam core having at least one sorbent disposed within said metal foam, said sorbent configured to selectively adsorb and desorb preselected materials at designated conditions, said metal foam further configured to have sufficient thermal conductivity whereby essentially uniform temperatures throughout said metal foam are obtained in response to heating or cooling; and
   a heater operatively connected to said tube and its contents whereby the temperature within said metal foam can be varied according to a preselected criteria.

2. The analytical system of claim 1, wherein the metal foam comprises nickel.

3. The analytical system of claim 1, wherein the metal foam comprises stainless steel.

4. The analytical system of claim 1, wherein the metal foam has a mean pore diameter of about 380 microns.

5. The analytical system of claim 1, wherein the metal foam comprises at least about 95% air by volume.

6. The analytical system of claim 1, wherein said sorbent is of a mesh size selected in the range from about 60 to about 80.

7. The analytical system of claim 1, wherein said sorbent is of a grain size selected in the range from about 170 microns to about 250 microns.

8. The analytical system of claim 1, wherein said sorbent comprises a member selected from the group of Tenax®, Carbotrap®, Carboxen®, Carbosieve®, carbon nanotubes, glass bead, polymers, molecular sieves, activated carbons, ceramics, aluminas, silicas, silica gels, polars, dessicants, and combinations thereof.

9. The analytical system of claim 1, wherein said preconcentrator is operatively connected to an analytical device selected from the group consisting of Surface Acoustic Wave sensor, Flexural Plate Wave Sensor, mass spectrometer, ion mobility spectrometer, sensor array, multivariate detector, flame ionization detector, chemical sensor, gas chromatograph, gas chromatographic detector, and combinations thereof.

10. The analytical system of claim 1, wherein said preconcentrator further comprises a temperature sensor operatively connected to said heater to perform controlled thermal desorption of said one or more vapors.

11. The analytical system of claim 1, wherein said preconcentrator is operatively connected to a detector for analysis of said one or more vapors desorbed therefrom said detector selected from the group consisting of sensor arrays, chemical sensors, gas chromatographs, mass spectrometers, ion mobility spectrometers, gas-chromatography detectors, and combinations thereof.

12. The analytical system of claim 1, wherein said preconcentrator is operatively connected to a gas chromatography detector selected from the group consisting of thermal conductivity detectors, electron capture detectors, flame ionization detectors, and combinations thereof.

* * * * *